(12) United States Patent
Burge

(10) Patent No.: US 7,170,608 B2
(45) Date of Patent: Jan. 30, 2007

(54) SIMPLIFIED ANALYTICAL APPARATUS FOR FIELD DEPLOYABLE MEASUREMENTS OF MOLECULAR ABSORBANCE AND FLORESCENCE

(76) Inventor: Scott Russell Burge, 8869 S. Myrtle Ave., Tempe, AZ (US) 85284

(*) Notice: Subject to any disclaimer, the term of this patent is extended or adjusted under 35 U.S.C. 154(b) by 0 days.

(21) Appl. No.: 10/336,452

(22) Filed: Jan. 2, 2003

(65) Prior Publication Data

US 2004/0258343 A1  Dec. 23, 2004

(51) Int. Cl.
*G01N 21/00* (2006.01)
(52) U.S. Cl. .................. 356/440; 356/436; 356/437
(58) Field of Classification Search ......... 356/436–440
See application file for complete search history.

(56) References Cited

U.S. PATENT DOCUMENTS

| | | | | |
|---|---|---|---|---|
| 3,809,913 A | * | 5/1974 | Prellwitz | 250/575 |
| 3,838,925 A | * | 10/1974 | Marks | 356/438 |
| 5,094,526 A | * | 3/1992 | Freud et al. | 356/28.5 |
| 5,116,759 A | * | 5/1992 | Klainer et al. | 435/287.2 |
| 5,241,367 A | * | 8/1993 | Grob et al. | 356/435 |
| 5,291,030 A | * | 3/1994 | Brors | 250/573 |
| 5,510,895 A | * | 4/1996 | Sahagen | 356/436 |

* cited by examiner

*Primary Examiner*—Gregory J. Toatley, Jr.
*Assistant Examiner*—Amanda Merlino

(57) ABSTRACT

The invention simplifies the apparatus for the analysis of organic and inorganic compounds in solutions and atmospheres, or particulates in atmospheres. The apparatus supports molecular fluorescence and absorption analyses of trace environmental contaminants. The design of the apparatus allows for deployment within the confines of a monitoring well or other locations of limited access. The primary advantages are the easy replacement and configuration of excitation sources and detectors to configure a sample chamber for a particular analysis while using mininal volumes of sample or reagent. Miminizing the volume of reagent used is a very important consideration in automated field analyses. The invention uses light emitting diodes (LEDs) and photodetectors coupled to fiber optics to reduce the complexity and cost of the optics and electronics of the measurement components. The invention allows for the automation of sampling, sample preparation and analysis of environmental contaminants in natural waters and particulates in atmospheres, i.e. bacteria spores. The composition of the walls of the sample chamber determines the type of sample, natural water or atmosphere, that can be analyzed by the apparatus.

10 Claims, 3 Drawing Sheets

SIMPLIFIED ANALYTICAL APPARATUS FOR FIELD DEPLOYABLE MEASUREMENTS OF MOLECULAR ABSORBANCE AND FLORESCENCE

BACKGROUND OF INVENTION

The typical ultraviolet-visible (UV-Vis) molecular absorption spectroscopic method requires the reaction of an analyte with a colorimetric reagent. The resulting solution is transferred into a cuvette and the cuvette placed into a spectrophotometer for the analysis of the analyte in the solution. The cuvette may be characterized as a removable sample reservoir of the spectrophotometer. This methodology is difficult to automate, restricts the path length, and the optical system and electronics are large and expensive. The instrumentation is not optimized for long-term use in the field.

A removable sample reservoir with detectors and sources embedded in the the walls of a cell containing the removable sample reservoir was disclosed in U.S. Pat. No. 5,107,133 by Klainer. The disclosure does simplify the optics and electronics over the typical UV-Vis methods, however, the method has a removable reservoir. The invention is not optimized for the automation of the sampling, sample preparation and analysis.

A chemical reservoir sensor for molecular absorption and florescence was disclosed in U.S. Pat. No. 5,116,756 by Klainer et al. The invention sought to eliminate the need for fiber optics and used excitation sources and detectors embedded in the walls of the chemical reservoir, The chemical sensing reagent was contained within the body of the chemical reservoir and the analyte introduced into the reagent. The analyte was introduced into the chemical reservoir using a variety of techniques including permeable membranes embedded in the walls of the sample reservoir.

The invention presented in this disclosure uses fittings containing the excitation source or detector or both. Fiber optics are used to transmit light from the excitation source into the interior of the sample cell. Fiber optics are used to transmit light from the interior of the sample chamber to the detector. The sample reservoir is not removal and the sensing reagent does not reside in the sample reservoir.

There are several commercially-available fiber optic fittings for connecting fiber optics to sample curvettes for spectroscopic analysis. However, the terminal end of the fiber optic is conducted to an excitation source or a detector, or grating spectrometer, using a second fiber optic fitting. This invention does not transmit light through the optical fitting. The optical fittings described in this invention has the excitation source or detector located within the fittings. The fittings transmit electrical signals, not optical signals, to external instrument components, i.e. amplifers, etc. The second major difference is the terminal end of the fiber optic fitting in this disclosure is actually placed into the solution being analyzed. The commercially-available fiber optic fittings usually terminate at the outer wall of a cuvette. Several advantages to this design include the mininaturization of the entire system, the path length may be adjusted and the problems associated with bending fiberoptics in areas of limited space are eliminated.

SUMMARY OF INVENTION

This invention automates sampling, sample preparation and analysis using small volumes of reagents. The invention is composed of a sample chamber allowing for the introduction and removal of samples and reagents. The UV-Vis excitation sources and detectors are located inside fittings with fiber optics for transmitting and receiving light from within the sample chamber. The fittings can be connected to the walls or end plates of the sample chamber. The orientation of the fittings determine the type of analyses to be performed. The analyses capable of being performed by this invention include molecular absorption and fluorescence. This allows the sample chamber to double as the analytical cell.

The ability to perform both sample preparation and analysis in the same sample chamber/analytical cell allows for the automation of the sampling, sample preparation and measurement process with mininal volumes. The selection of the material used for the fabrication of the wall of the sample chamber determines the type of sample that can be analyzed. Impermeable materials used in the fabrication of the walls of the sample chamber are suitable for the analysis of natural waters. Permeable materials used in the fabrication of the walls of the sample chamber are suitable for the analysis of particulates (i.e. bacteria spores) in atmospheres. An example of a permeable material would be an expanded fluorocarbon membrane (i.e. Gortex). This material is capable filtering atmospheres and capturing particulates on the interior wall of the sample chamber. After the capture of a sufficient concentration of particulates, a calorimetric or other reagent can be introduced into the sample chamber causing a reaction with the particulates. The resulting solution is then analyzed. One of the major properties of expanded fluorocarbon membranes is the ability of the membrane to be impermeable to solutions while passing vapors and air.

DETAILED DESCRIPTION OF THE PREFERRED EMBODIMENTS

The primary components of the invention are the sample chamber and various fiber optic fittings. The sample chamber serves as both the reaction and analytical cell. The material used in the construction of the sample chamber wall determines the type of sample that can be analyzed. The fiber optic fittings have several types of designs for supporting molecular florescence and absorption of molecules in atmospheres, solutions and airborne particulates. The placement of the fiber optic fittings on the end plates or walls of the sample chamber determine the type of analysis to be performed.

Figure 1:
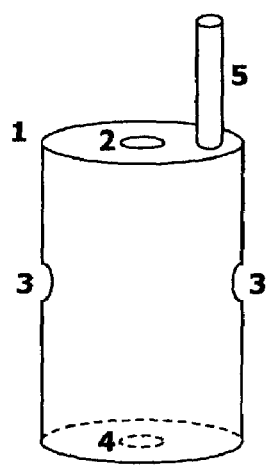
FIG. 1 is an illustration of the sample chamber/analytical cell with mounting ports for optical fittings.

FIG. 1 illustrates the sample chamber 1 with several possible locations for the analytical ports 2, 3, 4. The actual number and locations of the analytical ports 2, 3 4 are determined by the type of sample to be analyzed and the type of analyses to be performed. One or more inlet/outlet ports 5 are used for introducing samples and reagents into the interior of the sample chamber 1 for analysis and/or removing the analyzed samples from the sample chamber. All the analytical ports 2, 3, 4 are fitted with threaded holes or other means for connecting a fiber optic fitting 6 of FIG. 2. The analytical port 2 located at the top of the sample chamber 1 may be used in conjunction with an analytical port 3 located on the side of the sample chamber 1. Alternatively, The analytical port 2 located at the top of the sample chamber 1 may be used in conjunction with an analytical port 4 located on the bottom of the sample chamber 1. There are several embodiments only requiring the use of one analytical port.

The total volume of the sample chamber may be from 0.1 to 100 mL. The sample and reagent are introduced into the sample chamber 1 using one or more solution inlet/outlet ports 5. The volume of aqueous samples and reagents introduced in the sample chamber 1 is controlled by water level sensors or other methods of liquid volume control. The solution within the sample chamber may be agitated to aid in the completion of the reaction. After the completion of the reaction, the resulting solution is analyzed within the sample chamber 1. The sample chamber 1 couples as the analytical cell. This coupling of the sample chamber with the analytical cell allows for the use of small volumes of samples and reagents and can be easily automated.

The walls of the sample chamber 1 may be fabricated from permeable or impermeable materials. A sample chamber 1 with walls fabricated from impermeable materials may be used for the analysis of natural waters and other aqueous and non-aqueous solutions. A sample chamber 1 with walls fabricated from permeable materials such as expanded fluorocarbon membrane is used for the analysis of particulates in air or other atmospheres. The particulates are collected on the interior wall of the sample chamber 1 by the introduction of particulates suspended in air or other atmosphere through the inlet/outlet port 5 and the air allowed to pass through the permeable wall trapping the particulates. After a sufficient concentration of particulates are collected on the interior wall of the sample chamber 1, the air flow is terminated and a reagent, extraction fluid or other solution is introduced into the interior of the sample chamber 1 using the inlet/outlet port 5. There can be more than one solution inlet/outlet port 5 for introducing solutions into the interior of the sample chamber 1. The resulting solution of the particulate-reagent interaction is determined using molecular absorption, molecular fluorescence or other chemical/biological analytical methodologies.

Figure 2:
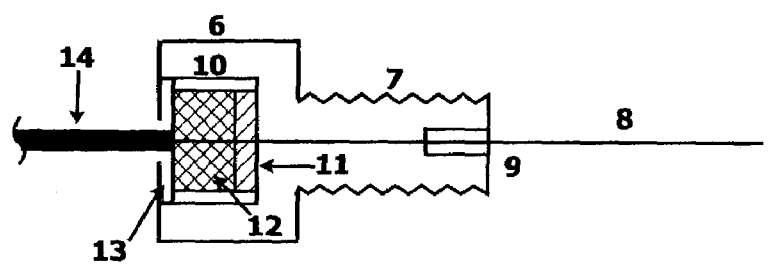
FIG. 2 is an illustration of an optical fitting with excitation source or detector.

FIG. 2 illustrates the basic fiber optic fitting 6. The basic fiber optic fitting is composed of screw threads 7 or other means of attaching the fiber optic component 6 to the sample chamber 1 with a seal. The fiber optic 8 is sealed into the body of the fiber optic fitting using a seal 7. The seal 9 may be an epoxy or other sealant, heat shrink fluorocarbon polymer or other material forming a seal between the fiber optic 8 into the fiber optic fitting 6. The fiber optic 8 is terminated in the excitation source/detector cavity 10. The excitation source/detector cavity 10 contains the excitation source or detector 12 and back plate 13 which is used to mount the excitation source/detector 12 into the fiber optic fitting 6. An optional optical filter 11 may be located between the excitation source or detector 12 and the fiber optic 8. An electrical cable 14 is used to connect the excitation source or detector 12 to the appropriate electronic components for signal manipulation.

The preferred excitation source 12 for the optical fittings are light emitting diodes (LEDs). The preferred detector 12 are solid state photodetectors. A preliminary design of this invention was tested for the determination of Cr(VI) using phenycarbazide employing a molecular absorbance technique. The two fiber optic fittings orientated along the same axis had a 4-cm path length.

The excitation source fitting used a green LED (540 nm) and the detector fitting used a Hammatsu photodetector. The analysis had a limit of detection of 5 parts per billion using a total volume of 5 ml of solution and reagent.

The fiber optic 8 is designed to pass beyond the end of the body of the iber optic fitting 6. The fiber optic 8 may have the cladding removed to prevent a reaction of the cladding with the reagent used to perform the analysis. The composition of the fiber optic fitting 6 is selected to prevent a reaction with the reagent being used in the analysis. The path length is determined by the separation of the terminal ends of the fiber optics 8 not the dimensions of the sample cell 1.

The fiber optic fittings 6 are attached to the sample chamber 1 to create the various analytical methods, molecular florescence or absorption, of the solution contained in the sample chamber 1.

Figure 3:
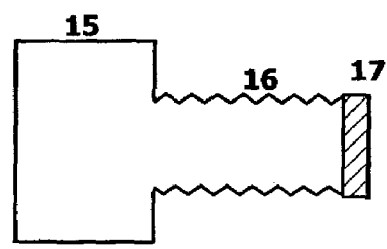
FIG. 3 is an illustration of a reflecting fitting.

FIG. 3 illustrates a blank fitting 15 which is used to plug the analytical ports which are either not in use or can be used to aid in the analysis. The blank fitting 15 is attached to the sample chamber 1 of FIG. 1 with the use of threads 16 or other means of attachment to the sample chamber 1. A mirror or other means of reflecting light 17 may be mounted on the blank body 15 which may be used to perform molecular absorbance measurements.

Figure 4:
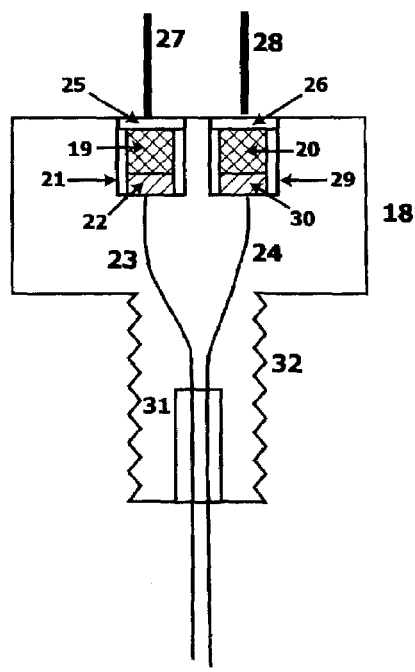
FIG. 4 is an illustration of optical fitting incorporating both the excitation source and detector.

FIG. 4 illustrates a dual fiber optic fitting 18. The detector 19 and excitation source 20 are mounted in the same fiber optic fitting 18. The detector cavity 21 can be fitted with an optional optical filter 22 which is placed closest to the terminal end of the detector fiber optic 23. The detector 19 is located between the detector end plate 25 and the optical filter 22. In some applications the optical filter 22 may not be required. The excitation source cavity 29 is fitted with an optional optical filter 30 which is placed closest to the terminal end of the source fiber optic 24. The excitation source 20 is located between the source end plate 26 and the optical filter 30. In some applications the optical filter 30 may not be required. The excitation source fiber optic 24 and the detector fiber optic 23 are passed through a seal 31 which allows the sufficient barrier between the dual fiber optic fitting 18 and the fiber optics 23, 24 to prevent leakage. The threads 32 or other method of attachment are used to attach the dual fiber optic body 18 to the sample chamber. The terminal ends of the excitation source fiber optic 24 and the detector fiber optic 23 are introduced directly into the sample being analyzed.

Figure 5:
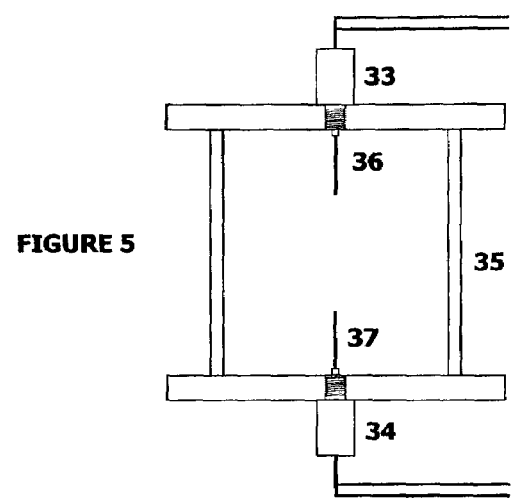
FIG. 5 is an illustration of sample chamber and optical fitting configuration for molecular absorbance measurements.

FIG. 5 illustrates the use of an excitation source fitting 33 aligned along the same axis as an detector fitting 34. The fittings 33, 34 are located on the opposite ends of a sample chamber 35. The light from the excitation source fitting 33 is transmitted through the excitation source fiber optic 36 to the interior of the sample chamber 35. The light, after passing through the solution is collected by the detector fiber optic 37 of the detector fitting 34. The alignment of the optical fittings allow for molecular absorbance measurements.

Figure 6:
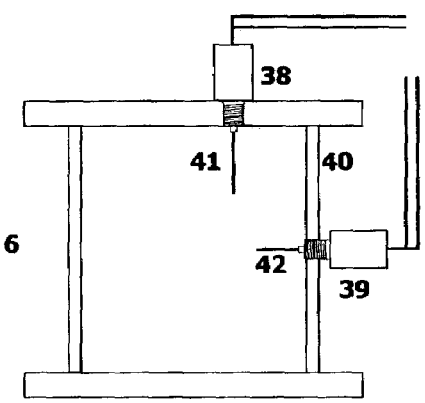
FIG. 6 is an illustration of sample chamber and optical fitting configuration for molecular florescence measurements.

FIG. 6 illustrates the use of an excatiation source fitting 38 aligned along a different axis than the detector fitting 39. The fittings 38, 39 are located at the top and side of the sample chamber 40. The light from the excitation source fitting 38 is transmitted through the excitation source fiber optic 41 to the interior of the sample chamber 40. The fluorescent light is collected by the detector fiber optic 42 of the detector fitting 39. The alignment of the optical fittings allow for molecular florescence measurements.

Figure 7:
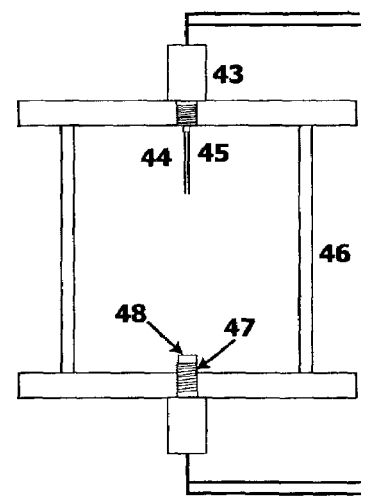
FIG. 7 is an illustration of sample chamber with a optical fitting incorporating both excitation source and detector and an optical fitting containing a reflecting surface for molecular absorbance measurements.

FIG. 7 illustrates the use of a dual optical fiber system with the excitation source and detector located in the same fitting 43. Molecular absorbance measurements are performed by fitting the opposite analytical port with a blank fiber optic fitting 47 fitted with a reflecting surface 48. The light emitted from the excitation source fiber optic 44 is reflected from the reflecting surface 48 on the blank fiber optic body 47 and collected by the detector fiber optic 45 which is used to measure absorbance of the species of interest in the sample. Molecular fluorescence measurements are performed by replacing the reflecting surface 48 of the blank fiber optic body 47 with a surface which does not reflect the excitation source light back into the detector fiber optic 45. The wavelength of the light from the excitation source fiber optic 44 is used to excite the molecule of interest in the media. Upon fluorescence, the light from the excited molecules is collected through the detector fiber optic 45.

Figure 8:
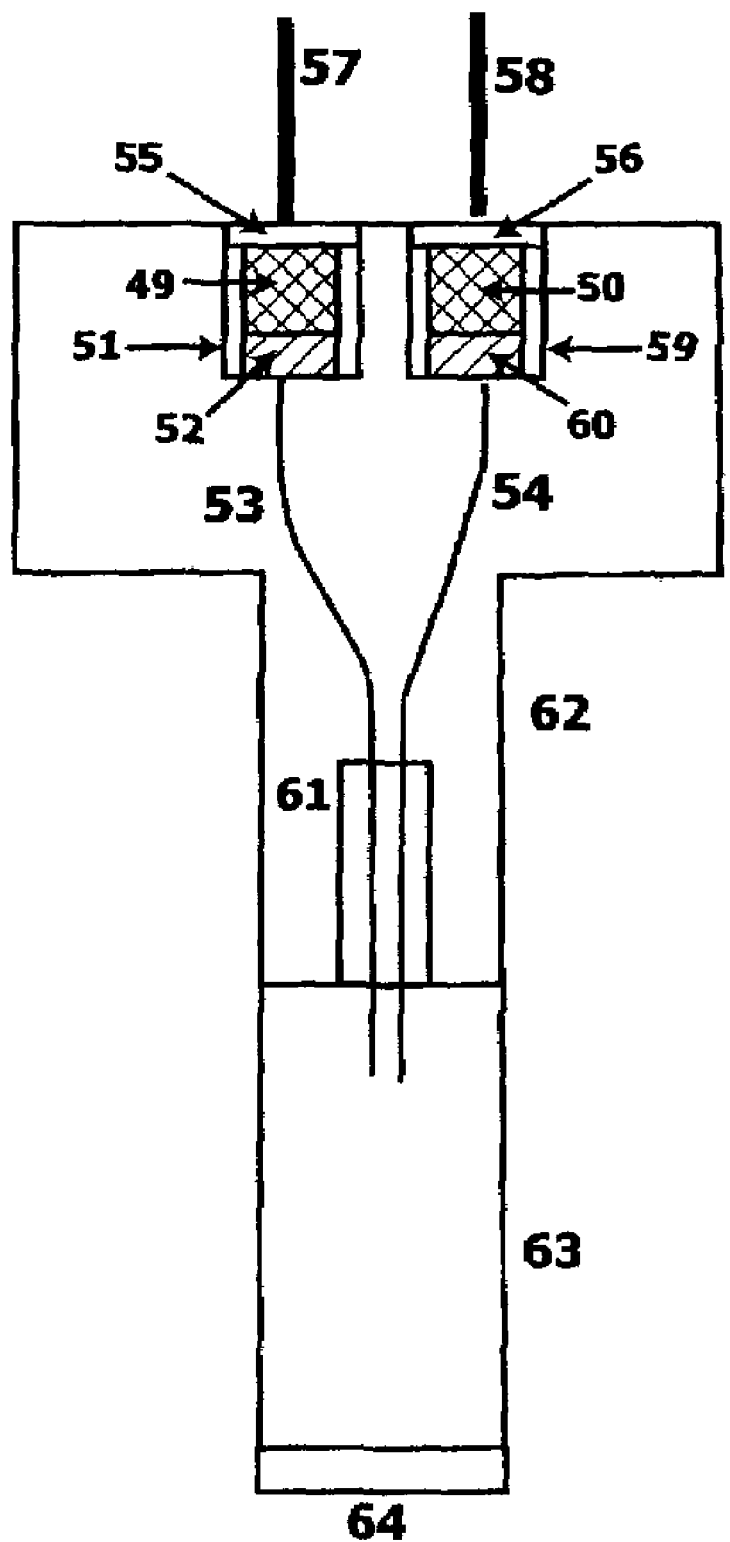
FIG. 8 is an illustration of an optrode incorporating the excitation source, detection and reflecting surface in one assembly.

FIG. 8 illustates an optrode for use in either a sample chamber 1 of FIG. 1 or for use as a replacement for a spectrophotometer for performing colorimetric analysis in the laboratory. The detector 49 and excitation source 50 are both mounted in the same optrode body 62. The detector cavity 51 is fitted with an optional optical filter 52 which is placed closest to the terminal end of the detector fiber optic 53. The detector 49 is located between the detector end plate 55 and the optical filter 52. In some applications the optical filter 52 may not be required. The excitation source cavity 59 is fitted with an optional optical filter 60 which is placed closest to the terminal end of the source fiber optic 54. The excitation source 50 is located between the source end plate 56 and the optical filter 60. In some applications the optical filter 60 may not be required. The excitation source fiber optic 54 and the detector fiber optic 53 are passed through a seal 61 which allows the sufficient barrier between the optrode body 62 and the fiber optics 53, 54 to prevent leakage. The terminal ends of the excitation source fiber optic 54 and the detector fiber optic 53 are introduced directly into the sample being analyzed. A reflecting surface 64 is suspended below the terminal ends of the excitation source fiber optic 54 and the detector fiber optic 53. The reflecting surface 64 is typically located 0.5 to 3 cm below the terminal ends of the fiber optics 53, 54. The reflecting surface 64 is used to reflect the light from the terminal end of the excitation source fiber optic 54 into the terminal end of the detector fiber optic 54.

The typical source used for the the excitation source 50 are LEDs. The typical detector 49 is solid-state photodetector. This optrode may be used independently of a sample chamber and can be used a substitute for a spectrophotometer in the colorimetric analysis of several analytes such as cobalt, chromoum (VI) and nickel.

I claim:

1. A chemical sensor comprising:
    a sample chamber having ports means extending through the walls of the sample chamber,
    a first fiber optic fitting having embedded therein optical signal means adapted for connection with said ports means to illuminate through a first optical fiber to the interior of said sample chamber,
    a second fiber optic fitting having a detector embedded therein and adapted for connection with said ports means to measure interaction of light through a second optical fiber to within the interior of said sample chamber wherein the ends of said first and second optical fibers extend past the end of the first and second optical fittings into the sample chamber, and
    at least one port means in the walls of the sample chamber, said port comprising means to convey samples or liquids into and from the sample chamber.

2. A chemical sensor according to claim 1 wherein said fiber second optic fitting has embedded therein a detector aligned along the same axis as the second fiber optic fitting.

3. A chemical sensor according to claim 1 wherein the walls of said sample chamber comprise a permeable membrane.

4. A chemical sensor according to claim 1 wherein the walls of said sample chamber comprise an impermeable wall.

5. A chemical sensor according to claim 1 wherein at least one port comprises means for introduction of reagents and solutions into the interior of said sample chamber.

6. A chemical sensor according to claim 1 wherein walls of said ports means of said sample chamber are threaded.

7. A chemical sensor according to claim 1 wherein said optical fittings are threaded for connection at said port means.

8. A chemical sensor according to claim 1 wherein said optical fittings comprise connectors for connection with said port means.

9. A chemical sensor comprising:
    a sample chamber having port means extending through the walls of the sample chamber,
    a fiber optic fitting having embedded therein optical signals means adapted for connection with said port means to illuminate through a first optical fiber to the interior of said sample chamber and having a detector embedded therein and adapted for connection with said port means to measure interaction of light through a second optical fiber within the interior of said sample chamber, wherein the ends of the optical fibers extend past the end of the fiber optical fitting into the sample chamber, and
    At least one port, in the walls of the sample chamber, said port comprising means to convey samples or liquids into and from the sample chamber.

10. A chemical sensor according to claim 9 and further comprising a reflecting surface disposed at the terminal end of said optical fitting.

* * * * *